United States Patent [19]

Buxton

[11] Patent Number: 4,682,977
[45] Date of Patent: Jul. 28, 1987

[54] APPARATUS FOR FOLDING SPACED SEGMENTS OF WEB MATERIAL

[75] Inventor: Gerald W. Buxton, Green Bay, Wis.

[73] Assignee: Paper Converting Machine Company, Green Bay, Wis.

[21] Appl. No.: 887,218

[22] Filed: Jul. 21, 1986

[51] Int. Cl.⁴ .............................................. B05B 1/14
[52] U.S. Cl. .................. 493/358; 493/418; 493/423; 493/441; 493/450
[58] Field of Search .............. 493/178, 179, 182, 357, 493/358, 418, 423, 441, 450

[56] References Cited

U.S. PATENT DOCUMENTS

| | | | |
|---|---|---|---|
| 3,913,464 | 10/1975 | Flaum | 493/179 |
| 4,500,316 | 2/1985 | Damico | 604/389 |
| 4,614,512 | 9/1986 | Capdeboscq | 493/423 |

Primary Examiner—Frederick R. Schmidt
Assistant Examiner—Robert Showalter
Attorney, Agent, or Firm—Tilton, Fallon Lungmus & Chestnut

[57] ABSTRACT

Apparatus for folding spaced segments of web material such as diapers having intermediate side flaps overfolded in the crotch portion making use of a vacuumized continuously moving belt system for gripping one surface of a planar web except for the flap portions and a frictionalized belt system aligned with the vacuumized belt system for engaging the other surface of the web to progressively fold the flap portions.

7 Claims, 8 Drawing Figures

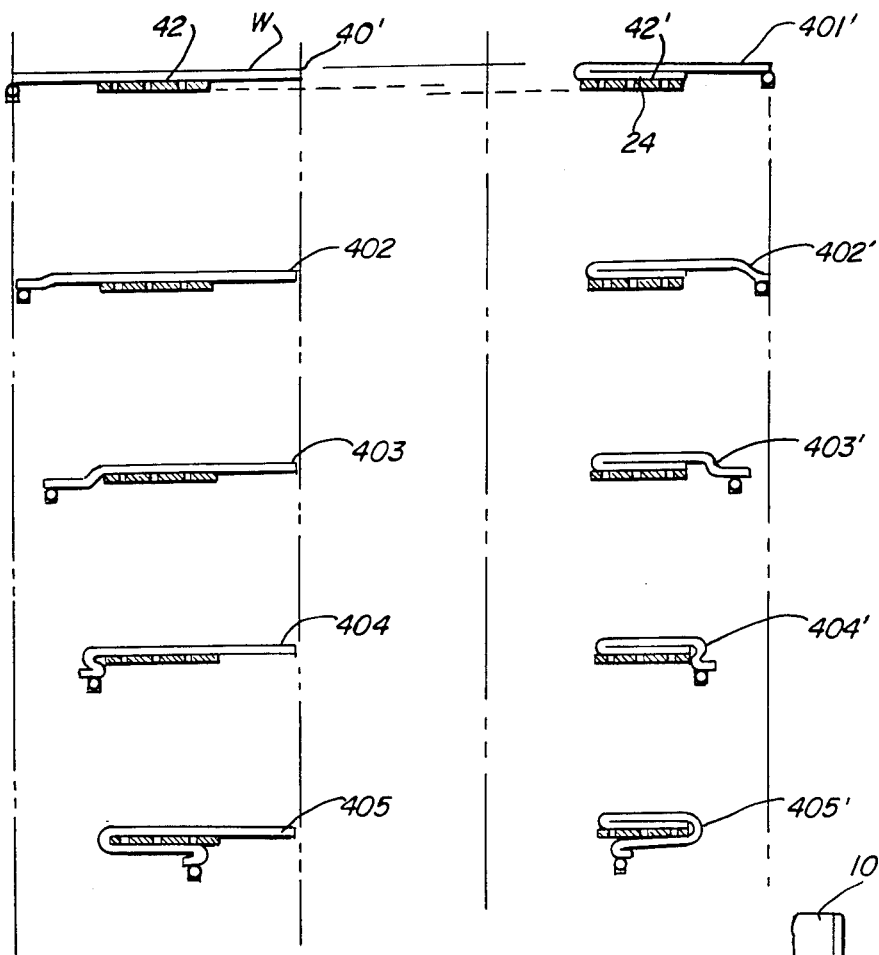

APPARATUS FOR FOLDING SPACED SEGMENTS OF WEB MATERIAL

BACKGROUND AND SUMMARY OF INVENTION

This invention relates to apparatus for folding spaced segments of web material and, more particularly, to apparatus for the production of disposable articles which embody folding a side flap inwardly.

Folding of an article such that two outer panels are folded inwardly and are superposed on the top or bottom of a central panel is a well-known practice, but it is limited to longitudinal folds where folding of the side margins is made while the continuous web is moving.

For special disposable products, for example, an incontinent pad or garment similar to the disposable article in U.S. Pat. No. 4,500,316, it is desirable to have a discreet marginal portion of "flap" overfolded from both sides to add significantly to the absorption capacity of the central "crotch" portion. Folding of the side panels which are severed approximately ⅓ of the web width from a marginal edge cannot be accomplished continuously or by means of conventional folding boards because the web is no longer continuous but is cut into predetermined segmented side flaps or panels which must be folded individually.

For the incontinent pad of '316, the flap portion on each side is folded toward the center and is superposed on the central absorption pad, thus increasing its thickness and absorption capacity approximately three times, and this desirable folding enhances the function and utility of said pad.

In order to fold discrete segments or side flaps, a phased device must be used to fold the side flap inwardly from each side, but prior art does not teach how discreet web portions can be folded inwardly while moving, nor does it teach mechanical elements which can grip and transfer said flaps. Additionally, there are no prior art teachings which relate to control of the central pad portion while the side folds are being made. The inventive device, therefore, teaches "C" folding of side web segments (flaps) toward the central portion of an absorbent pad and the like while the central portion is held and controlled to prevent transverse movement.

While the inventive device is particularly useful to selectively fold side portions of the web as defined in Patent '316, the method and device can be useful to complete an overlapped "C" fold for other disposable products made from a web which is partially continuous and partially severed on one or both sides in a repeating fashion to form flaps.

According to the invention, a vacuumized continuously moving belt means selectively grips one surface of the continuous web while a frictionalized continuously moving belt system engages the opposite surface of the web, the frictionalized belt system being arranged at an angle to the path of movement of the web to progressively fold flap portions while the web material is advancing in the path.

Other objects and advantages of the invention may be seen in the details set forth in the ensuing specification.

The invention is described in conjunction with the accompanying drawing, in which FIG. 1 is a fragmentary perspective view of the portion of the apparatus featuring the previously mentioned vacuumized belt and frictionalized belt system;

FIG. 4 is a series of schematic representations showing the progress of the two flap folding operations;

FIG. 5 is a side elevational view of one of the frictionalized belt systems such as would be seen along the sight line 5—5 applied to FIG. 3;

FIG. 6 is a top plan view, essentially schematic, of the belt of FIG. 5;

FIG. 7 is a side elevational view of the belt of FIG. 6; and

FIG. 8 is an enlarged end view of one of the friction elements provided on the frictionalized belt system.

DETAILED DESCRIPTION

The invention is described in conjunction with the illustrative embodiment which features a pad generally designated P which is constructed according to the teachings of U.S. Pat. No. 4,500,316. This can be seen in the right hand portion of FIG. 3 being provided as part of a web W also seen in FIG. 1.

The pad is equipped with cuts C and D extending generally transversely partway across the web from a longitudinally extending edge E of the web. These are adapted to be folded over the remainder of the web along a line of potential folding F. For further details of this diaper construction, kindly refer to the above mentioned '316 patent.

Figure 3:
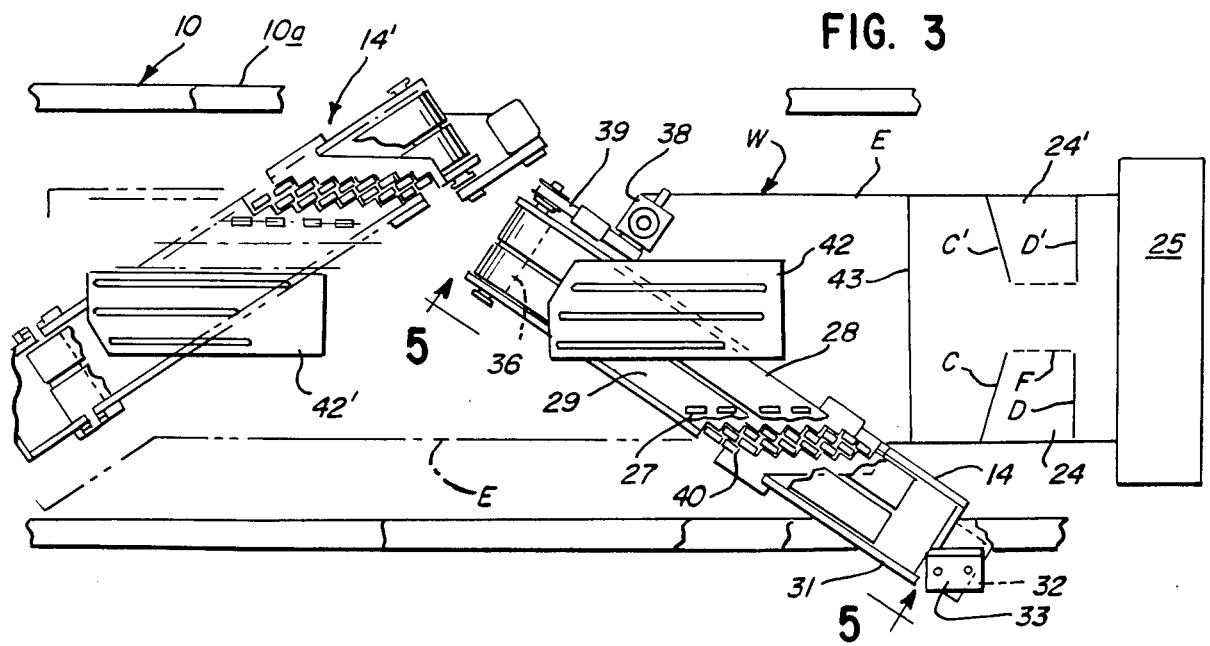
FIG. 3 is a top plan view of the two frictionalized belt systems which operate in conjunction with the vacuumized belt means.

The inventive apparatus incorporates a frame generally designated 10—now referring to the left hand portion of FIG. 3—which in conventional fashion has a pair of side frames on which the various rolls and other elements are mounted. It will be appreciated that in the high speed production of web products from a continuous web, it is essential to utilize rotary motion as much as possible so as to eliminate inefficient reciprocal motions. Therefore, such equipment normally embodies rolls journalled in side frames for the continuous advancement of a web. Also, as is normal practice, the frame supports advancing roll means as at the points 11 and 12 and such would be provided both upstream and downstream of the vacuumized belt system or means generally designated 13 in FIG. 1. The web W is illustrated as being advanced to the left in FIG. 1 as indicated by the arrow in the extreme left hand portion.

Figure 1:
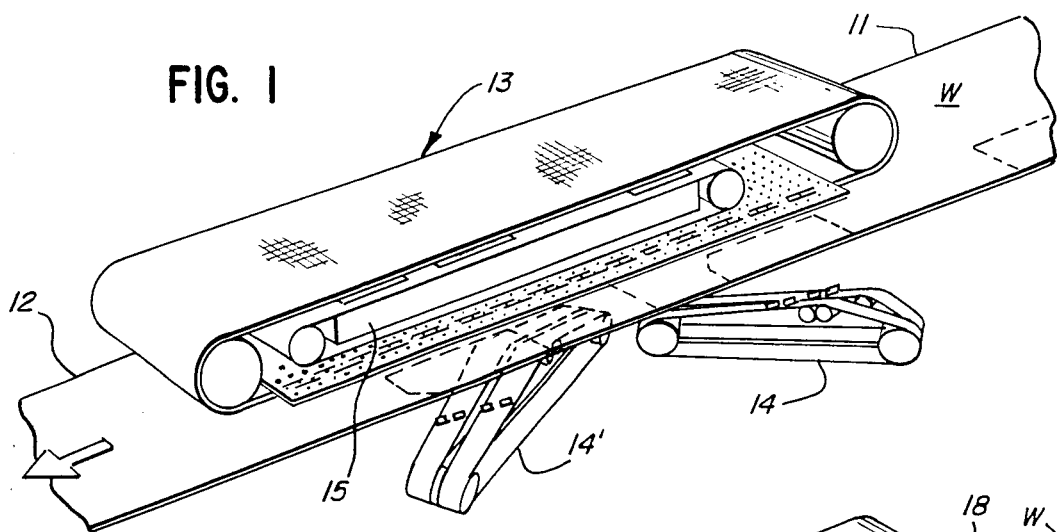

In FIG. 1, the inventive folding mechanism is illustrated with the vacuumized belt system 13 above the web W and two frictionalized belt systems 14 and 14' below the web W. Inasmuch as the web W is under complete control during the folding operation, the belt means and belt systems can be reversed and, for that matter, the web can be oriented vertically or at an angle as contrasted to the horizontal orientation shown.

Vacuumized Belt Means

Figure 2:
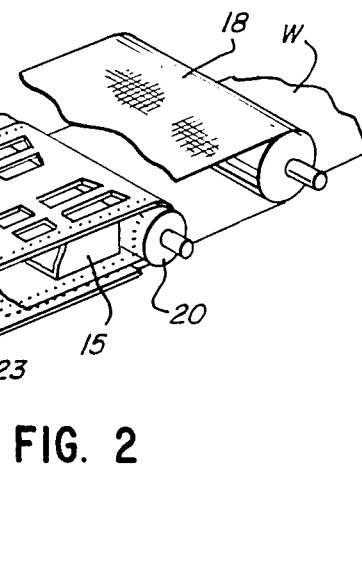
FIG. 2 is a view similar to FIG. 1 but with certain parts removed to better illustrate the vacuumized belt means.

In the illustration given, and with reference now to FIG. 2, vacuum is applied to the bottom surface of belt means 13 by means of a plenum chamber 15. This is internally vacuumized by means of conduits 16 coupled to a vacuum pump (not shown). The vacuumized belt system includes a pair of endless belts 17 and 18. As can be readily appreciated from a consideration of FIG. 2, the belt 17 is inside of the belt 18.

Selectively closing the open bottom of the plenum chamber 15 is the continuous belt 17 which is equipped with sprocket holes 19 engaging pins on the head and tail sprockets 20. It will be noted from FIG. 2 that the continuous inner belt 17 is equipped with a number of cutouts as at 21 which allow vacuum to be applied to portions of the web which are not to be folded.

Vacuum blanking portions 22 are impermeable and are phased to overlay portions of the web that will be subsequently folded, i.e., flap portions 24 and 24'. On the other hand, the cutouts or openings 21 permit vacuum to be applied to the rest of the web so as to maintain it under control.

Completing the assembly of the vacuumized belt system 13 is a perforated plate 23 which is supported by the frame 10 and is interposed between the continuous belts 17 and 18. The perforated plate insures that the continuous belt 18 which is advantageously of screen material, is not sucked into the plenum chamber 15. Suitable rails (not shown) are provided as part of the plenum chamber 15 to prevent sucking therein of the endless belt 17.

Flap Development

The flaps are designated 24 and 24' and are so designated in the right hand portion of FIG. 3. Ultimately the flap 24' will be underfolded by the frictionalized belt system 14' while the flap 24 will be underfolded by the frictionalized belt system 14.

To develop the flaps, a die roll pair 25—still referring to the extreme right hand portion of FIG. 3, is employed upstream of the belt means 13 and belt systems 14, 14'. This provides the transverse cuts C, D and C', D'. Depending upon the location of the die rolls 25—which are vacuumized to maintain the flaps 24, 24' in alignment with the rest of the web W, I can provide other vacuumized rolls to maintain the flaps in alignment until under the control of the belt system 13. It will be appreciated that at this juncture, the web is made up of a tissue or non-woven carrier sheet and a substantial layer of cellulosic fluff. Thus, there is some substantial weight in the flap which might tend to cause it to part from its desired aligned relationship during advancement into the folding station underneath the vacuumized belt means 13.

Frictionalized Belt Systems

For folding "on the fly", I employ a pair of frictionalized belt systems 14, 14'. These are essentially identical—with the system 14 being the one upstream and first encountering the web W so as to underfold the flap 24. The description will be essentially in terms of the system 14 for brevity.

First, it will be noted that the system 14 is arranged at an angle to the path of advancement of the web W. This is advantageously of the order of about 30° and to provide the continuously moving system 14 with a component of motion parallel and equal to that of the web W, I operate the frictionalized belt system 14 at a speed higher than the speed of advancement of the web W. This speed is related to the speed of the web by the secant of the acute angle at which the belt system 14 is arranged relative to the path of travel of the web W. Thus, the frictionalized belt system moves in synchronism with the web W but also has a transverse component useful in folding the flaps 24.

The frictional engagement of the web W is accomplished through a plurality of friction or gripping elements 27 partially covered with gripping material 26 (see FIG. 8). This material has inwardly facing hook-shaped fibers that interlock with the fibers of the web substrate and can be advantageously made of Velcro ®. These elements 27 outstand from a pair of belts 28 and 29—see the lower central portion of FIG. 3. FIGS. 6 and 7 illustrate schematically how the elements are positioned and outstand from the belt 28, it being understood that belt 29 is identically constructed. However, the belts 28 and 29 are offset so as to have the four elements aligned as seen in FIG. 3. Each belt has two sets of grippers, the second set being designated 27a in FIGS. 6 and 7. The sets are spaced apart equal distances upstream and downstream from each other. Each element 27 is provided on a suitable mounting base 30 as seen in FIG. 8.

Operation of Grippers

The grippers 27 engage the flap 24 along lower edge E (as illustrated in FIG. 3) and, for this purpose, are elevated slightly to insure engagement. This can be appreciated from a consideration of FIG. 5 which shows the two belts 28 and 29 and the structure for moving and supporting them.

Referring now to FIG. 5, the frictionalized belt system 14 is supported on a sub-frame 31. This is essentially an open rectangle as can be appreciated from a consideration of FIG. 3. The sub-frame 31 is rigidly connected to the frame 10 by brackets 32 and 33. At the left hand end a bracket 34 supports the sub-frame 31 from a cross spacer 35 extending between the side frames of the frame 10. The subframe rotatably supports a head pulley 36 and a tail pulley 37. Power for the head pulley 36 is provided by a right angle gear box 38 through a belt drive 39.

To provide the elevation of the belts 28 and 29, the subframe 31 supports a plurality of roller supports 40 and 41 (please compare the lower right hand portion of FIG. 3 with the upper right hand portion of FIG. 5). These are positioned between the head and tail pulleys and within the looped belts 28 and 29. Each of the support rollers is mounted with its axis of rotation extending perpendicular to the length of the belts 28 and 29 and these axes are offset to align the roller peripheries along the longitudinal edge E.

As the belts 28 and 29 move to the left in FIG. 5, their elevation is progressively decreased away from the zenith points defined by the rollers 40 and 41. This accommodates the underfolding which will now be described in conjunction with FIG. 4.

The sequence of folding for the system 14 is illustrated in the left schematic column of FIG. 4. The uppermost showing which is designated 401 shows the arrangement of the web W and the gripper 27 at the point of initial engagement, viz., at the synchronized zenith points provided by the rollers 40 and 41. The central portion of the web W is supported on a slotted plate 42 underwhich the fold will be developed as seen in the sequential views 402, 403, 404 and ultimately, 405.

The plate 42 is advantageously supported from the side frame 10a (see FIG. 3). This arrangement therefore does not interfere with the movement of the belt system 14. In FIG. 3, it will be noted that the plate 42 has a series of longitudially extending slots which are provided to maintain vacuum on the central web portion traveling underneath the plate 42 to prevent transverse displacement.

In the right hand portion of FIG. 4, a similar sequence of views are seen and which are designated 401', 402', 403', 404' and 405'. These picture the various stages of the second underfold developed from the flap 24'. It will be noted that the central plate 42' is at a lower elevation than that of the plate 42 so as to accommodate the additional thickness of web material developed by folding of the flap 24.

In the illustration given, individual pads are formed by transverse cuts 43 made prior (upstream) of die rolls 25. However, the folding techniques herein described can be used to fold portions of side margins of continuous webs that are not severed across the full web width and also the web can be severed transversely after edge folding is completed.

While in the foregoing specification a detailed description of an embodiment of the invention has been set down for the purpose of explanation, many variations can be made in the details hereingiven without departing from the spirit and scope of the invention.

I claim:

1. Apparatus for folding spaced segments of flexible web material comprising a relatively elongated frame, means on said frame for advancing a web along a linear path, said web having upper and lower opposite surfaces,
   means in said web path for generally transversely cutting said web partway across from a longitudinally extending edge at longitudially spaced lines to develop foldable flap portions each having a longitudially extending free edge,
   a vacuumized continuously moving belt means down stream in said path from said cutting means for selectively gripping said upper surface of said web except for said flap portions,
   a frictionalized continuously moving belt system aligned in said path with said vacuumized belt means for engaging said lower surface of said web, said frictionalized belt system being arranged at an angle to said path to progressively fold said flap portions while said web material is advancing in said path and having its speed related to the speed of said advancing means by the secant of said angle, said frictionalized belt system including gripper means for folding each flap portion commencing adjacent said longitudinally extending free edge and generating a line of folding moving progressively inward from said longitudinally extending free edge.

2. The apparatus of claim 1 in which two frictionalized belt systems are provided for folding sequentially flap portions from opposite longitudinal side edges of said web material.

3. The apparatus of claim 1 in which said frictionalized belt system includes roller support means in alignment with said longitudinal edge for urging said frictionalized belt system into engagement with said web flap portions.

4. The apparatus of claim 3 in which said frictionalized belt system includes a subframe providing spaced apart pulleys and an endless belt looped around said pulleys, said roller support means being positioned between said pulleys and within said loop belt to urge the same outwardly.

5. The apparatus of claim 4 in which said roller support means include a plurality of individual rollers each journalled on said sub-frame for rotation about an axis perpendicular to the direction of belt motion, said rollers having axes offset to align the roller peripheries along said longitudinal edge.

6. The apparatus of claim 1 in which said frictionalized belt system includes a plurality of outstanding hook type grippers.

7. The apparatus of claim 1 in which said vacuumized belt means includes a plenum chamber having an open face, a continuous moving belt about said plenum and partially closing said face and having selective portions cut out of said belt to applying vacuum to said web in non-flap portions thereof.

* * * * *